US006451304B1

(12) United States Patent
Friedmann et al.

(10) Patent No.: US 6,451,304 B1
(45) Date of Patent: Sep. 17, 2002

(54) **METHOD FOR RETROVIRUS VECTOR PRODUCTION BY SEPARATED *GAG* AND *POL* EXPRESSION**

(75) Inventors: Theodore Friedmann, La Jolla; Atsushi Miyanohara, San Diego, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/265,013

(22) Filed: Mar. 9, 1999

Related U.S. Application Data
(60) Provisional application No. 60/077,625, filed on Mar. 9, 1998.

(51) Int. Cl.[7] .............................................. A01N 63/00

(52) U.S. Cl. .................. 424/93.2; 435/69.1; 435/93.2; 435/235.1; 435/236; 435/320.1; 435/455; 435/456; 435/465; 435/466; 514/44; 536/23.1; 536/23.72

(58) Field of Search ............................... 435/69.1, 93.2, 435/235.1, 236, 320.1, 455, 55, 56, 57, 70, 71, 456, 465, 466; 514/44; 536/23.1, 23.72; 424/93.2

(56) References Cited

U.S. PATENT DOCUMENTS 5,672,344 A 9/1997 Kelley et al. ............... 424/93.2

FOREIGN PATENT DOCUMENTS

| WO | WO 95/30763 | 11/1995 |
| WO | WO-9712622 A1 * | 4/1997 |

OTHER PUBLICATIONS

Markowitz et al. Construction and use of a safe and efficient amphotropic packaging cell line. Virology (1988) vol. 167, pp. 400–406.*
Naldini et al. In vivo gene delivery and stable transduction of nondeviding cells by a lentiviral vector. Science (1996) vol. 272, pp. 263–267.*
Desrosiers, R., et al, "Synthesis of Bovine Growth Hormone in Primates by Using a Herpesvirus Vector," *Mol and Cell Bio*, Oct. 1985;2796–2803.
Markowitz, et al., "Construction of a safe packaging line for use in gene transfer with retroviral vectors," *J of Cell Biochem*, Jan. 30–Feb. 26, 1988;Supp 12B:181. (Abstract).
Markowitz, et al., "Retroviral Gene Transfer using Safe and Efficient Packaging Cells Lines," *Annals of the N.Y. Acad of Sci*, 1990;612:407–414.
Miyanohara, et al., "Efficient expression of retroviral vector–transduced human low density lipoprotein (LDL) receptor in LDL receptor–deficient rabbit fibroblasts in vitro," *Proc Natl Sci USA*, 1988;85:6538–6542.
Richardson, J., et al., "Helper Virus–free transfer of human immunodeficiency virus type 1 vectors," *J of Gen Vir*, 1995;76:691–696.
Soneoka, Y., et al., "A transient three–plasmid expression system of the production of high titer retroviral vectors," *Nucl Acids Res*, 1995;23(4):628–633.

* cited by examiner

Primary Examiner—Alfred Stucker
Assistant Examiner—Ulrike Winkler
(74) Attorney, Agent, or Firm—Foley & Lardner (57) ABSTRACT

The invention provides a system for production of retroviruses which are replication incompetent. In the system, gag and pol retroviral structural proteins are expressed separately by different plasmids in a packaging cell line. Separate gag and pol expressing plasmids are provided, as are packaging cell lines containing such plasmids. Retrovirus products of the retroviral vector production system, including chimeric retroviruses, are also provided.

16 Claims, 5 Drawing Sheets

METHOD FOR RETROVIRUS VECTOR PRODUCTION BY SEPARATED *GAG* AND *POL* EXPRESSION

RELATED APPLICATIONS

This application is based on and claims priority to U.S. provisional application, Serial No. 60/077,625, filed on Mar. 9, 1998, now abandoned.

BACKGROUND FOR THE INVENTION

1. Field of the Invention

The invention relates to retrovirus vectors for use in the expression of recombinant proteins and peptides. In particular, the invention relates to a method for producing retrovirus vectors using separate genes for the gag, pol and env structural retrovirus genes.

2. History of the Prior Art

Retroviruses which can accept and express foreign genes (e.g., the Moloney murine leukemia virus (MoMLV)) are useful in a number of applications, including gene therapy. However, since recombinant retroviruses are defective, they require assistance in order to produce infectious vector particles. This assistance can be provided by using helper virus carrying packaging cell lines that include structural genes of the retrovirus (e.g., env, gag and pol) under the control of regulatory sequences.

The use of retroviral vectors to deliver encoded material to a host raises the possibility that recombination of the genes provided by the vector virus and helper virus can occur to produce a replication-competent virus capable of infecting the host with viral proteins. Separation of the helper virus gag/pol and env encoding genes onto two separate plasmids in the packaging cell line (one which codes for the viral gag/pol proteins and another which does for the viral envelope protein) makes this possibility more remote by requiring that at least two recombination events occur for a replication-competent retrovirus (RCR) to be produced. Removal of the ψ packaging sequence from the plasmids also helps to reduce the risk of RCR infection. This arrangement significantly decreases, but does not eliminate, the incidence of RCR production by retrovirus packaging cell lines.

SUMMARY OF THE INVENTION

The invention is directed to a method for producing replication-incompetent retroviral (RIR) vectors. The vectors are produced according to the invention using packaging cell lines in which the helper virus gag, pol and env genes are each separated onto different provirus plasmids; i.e., one which codes for the viral gag protein, another which codes for the viral pol protein and a third which codes for the viral envelope protein.

To this end, the invention provides provirus plasmids which separately code for gag, pol and envelope proteins (respectively, pGag, pPol and pEnv), as well as a packaging cell line transfected with the plasmids for use in producing RIR vectors.

RIR vector products of the method of the invention are also provided by the invention. In one aspect, such RIR products are formed from a packaging cell line in which pGag and pPol provirus plasmids code for viral proteins from the same parent retrovirus.

In another aspect, RIR products are formed from a packaging cell line in which the pGag and pPol provirus plasmids code for viral proteins from different parent retroviruses.

The invention also provides packaging cell lines in which expression of one or more of the gag, pol and envelope proteins is enhanced by the addition of, respectively, pGag and pPol.

DETAILED DESCRIPTION OF THE INVENTION

Figure 1:
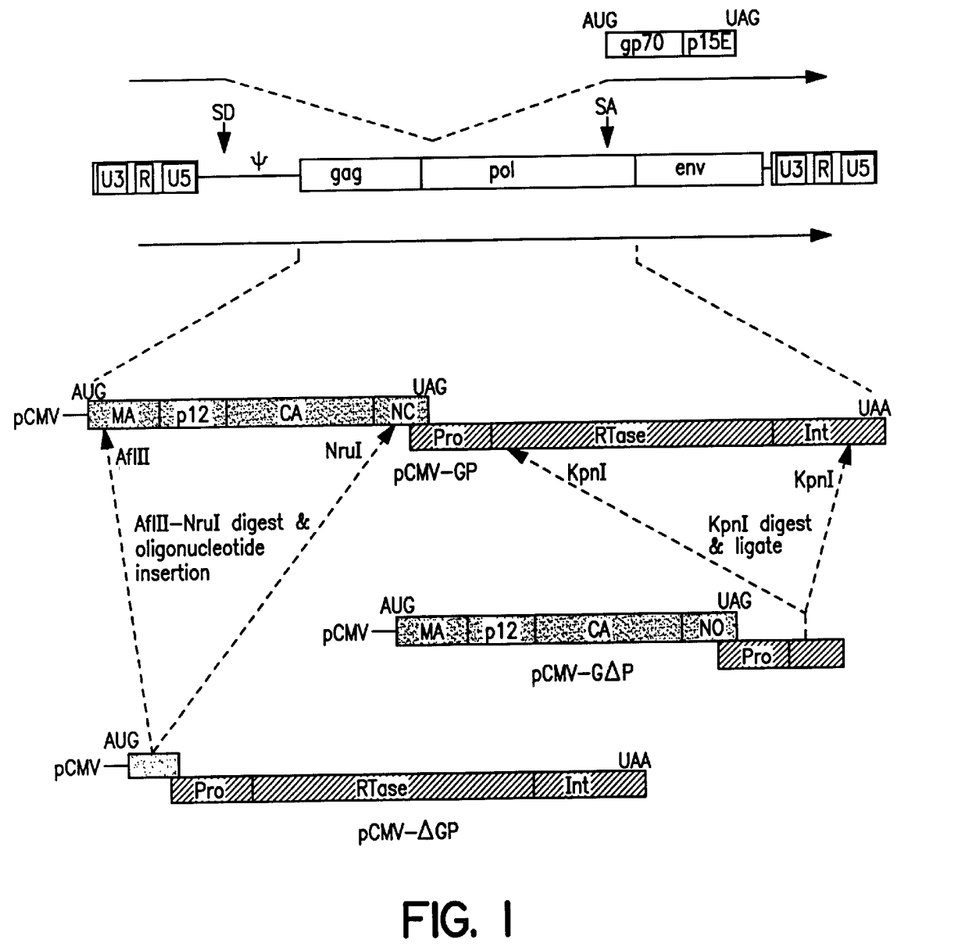
FIG. 1 is a schematic representation of steps leading to the production of a plasmid (pCMV-GΔP) which codes for MoMLV gag, but not pol.
Figure 2:
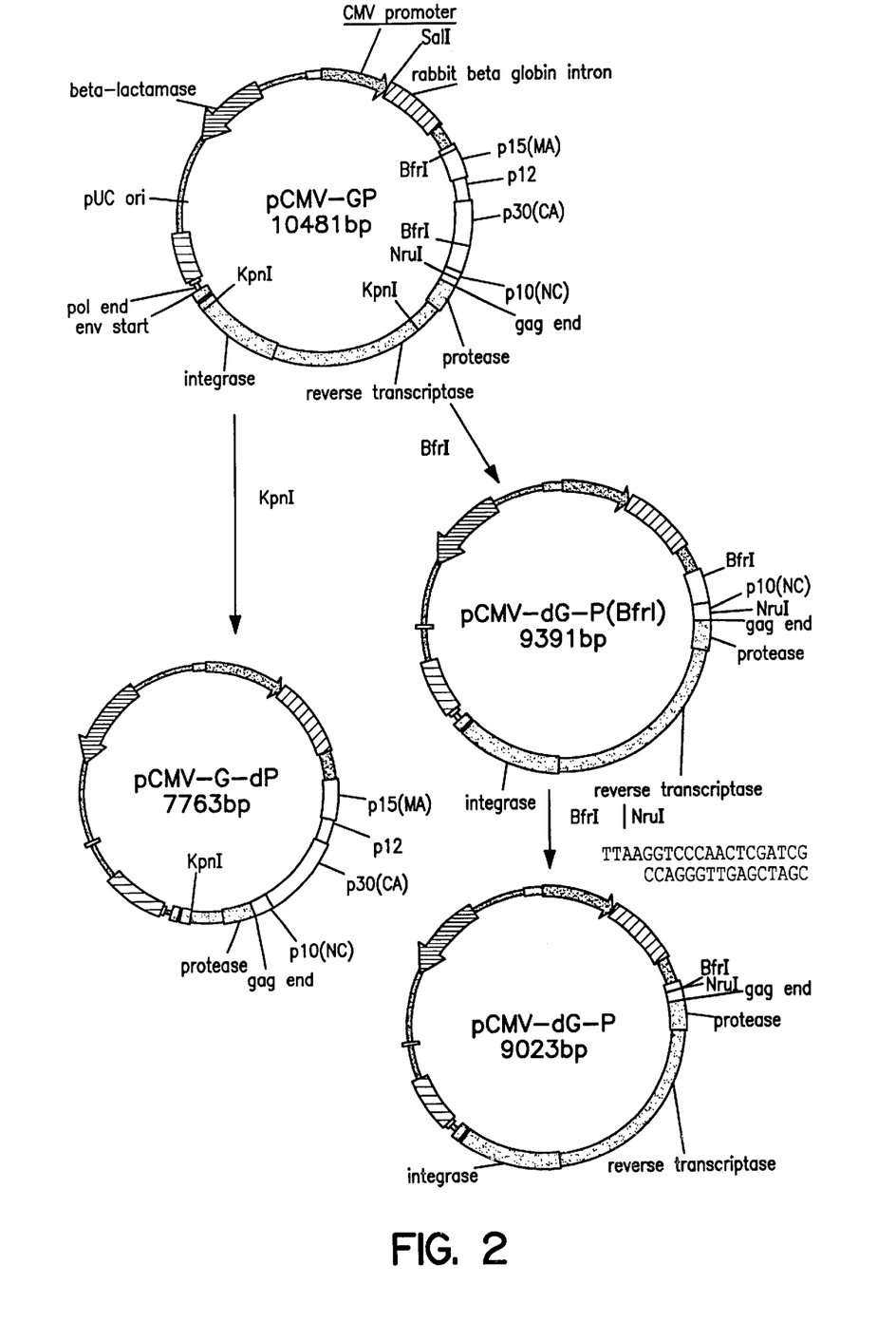
FIG. 2 is a schematic representation of steps leading to the production of a plasmid (pCMV-ΔG-P) which codes for MoMLV pol, but not gag.

FIGS. 1 and 2 schematically depict the steps employed to construct provirus plasmids which separately express gag and pol viral proteins. As shown in FIG. 1, the gag-only expressing provirus plasmid (pCMV-GΔP), and pol-only provirus plasmid (pCMV-ΔG-P), 5 were constructed using a gag-pol expressing plasmid (pCMV-GP) as a starting material. pCMV-GP expresses the Moloney murine leukemia virus (MoMLV) gag-pol genes from the immediate early promoter-enhancer of the human cytomegalovirus. pCMV-GP is constructed by inserting a 5.5 kb DNA fragment encoding the MoMLV gag-pol proteins into the EcoRI restriction site of the plasmid pCMV-Bam.

The MoMLV gag-pol encoding DNA sequence consists of nucleotides 368-58837 of the MoMLV genomic nucleotide sequence (reported in *RNA Tumor Viruses*, Vol. 11, Cold Spring Harbor Laboratories, 1985; GenBank Accession No. J02255; SEQ.ID.NO. 1). Those of ordinary skill in the art will appreciate that other expressible retroviral polynucleotides (i.e., polynucleotides in operable linkage with regulatory and control sequences, such as promoters, to operably express the encoded retroviral gene) may be used to construct provirus plasmids for use in the invention (preferably from murine or avian retroviruses), such as the murine sarcoma virus (e.g., GenBank No. V01185); Friend murine leukemia virus (e.g., GenBank No. Z 11128); murine osteosarcoma virus (e.g., GenBank No. K02712); other murine type C retroviruses (e.g., GenBank No. X94150); CAS-BR-E murine leukemia virus (e.g., GenBank No. X57540); avian IC10 retrovirus (e.g., GenBank No.13744); rous sarcoma virus (e.g., GenBank No. ALRDA), avian leukosis virus (ALV) and HIV.

In the MoMLV genome, the gag gene is at nucleotides 621–2237 and the pol gene is at nucleotides 2223–5834. pCMV-Bam is described in Yee, et al., *Proc. Nat'l. Acad. Sci USA*, 91:9564–9568 (1994). Each of these references are incorporated herein to exemplify sources of knowledge concerning gag-pol encoding nucleotides and promoter sequence-containing plasmids. Using pCMV-GP as the starting material, pCMV-GΔP is constructed by removing most of the pol gene (SEQ.ID.No. 3) from the plasmid by digesting the plasmid with the KpnI restriction endonuclease. The pol sequence is thusly cut at nucleotides 2858 and 5576. The remaining pol gene sequence is religated in-frame to the original coding frame as shown in FIG. 1.

Using pCMV-GP as starting material, pCMV-ΔG-P is constructed by removing most of the gag gene (SEQ.ID.No. 2) from the plasmid by digesting the plasmid with the restriction endonucleases AflII and NruI. The gag sequence is thusly cut at nucleotides 645 and 2122. Once this portion of the gag sequence is removed, it is replaced by the insertion of the following synthetic oligonucleotides corresponding to the 5' TTAAG sequence of AflII and the nucleotide sequence for NruI through the 3' TCG terminus using well-known, conventional ligation techniques:

TTAAGGTCCCAACTCGATCG (SEQ.ID.No. 4)

and

CCAGGGTTGAGCTAGC (SEQ.ID.No. 5)

Conveniently, the synthetic oligonucleotides of SEQ.ID. Nos. 3 and 4 serve to link pol to the start codon (ATG) for gag.

Expression of gag from pCMV-GP and pCMV-GΔP was confirmed by transfecting human kidney cell line 293 cells and detecting expressed protein using an anti-MoMLV antibody. gag gene expression was confirmed in all transfected cells.

Figure 3:
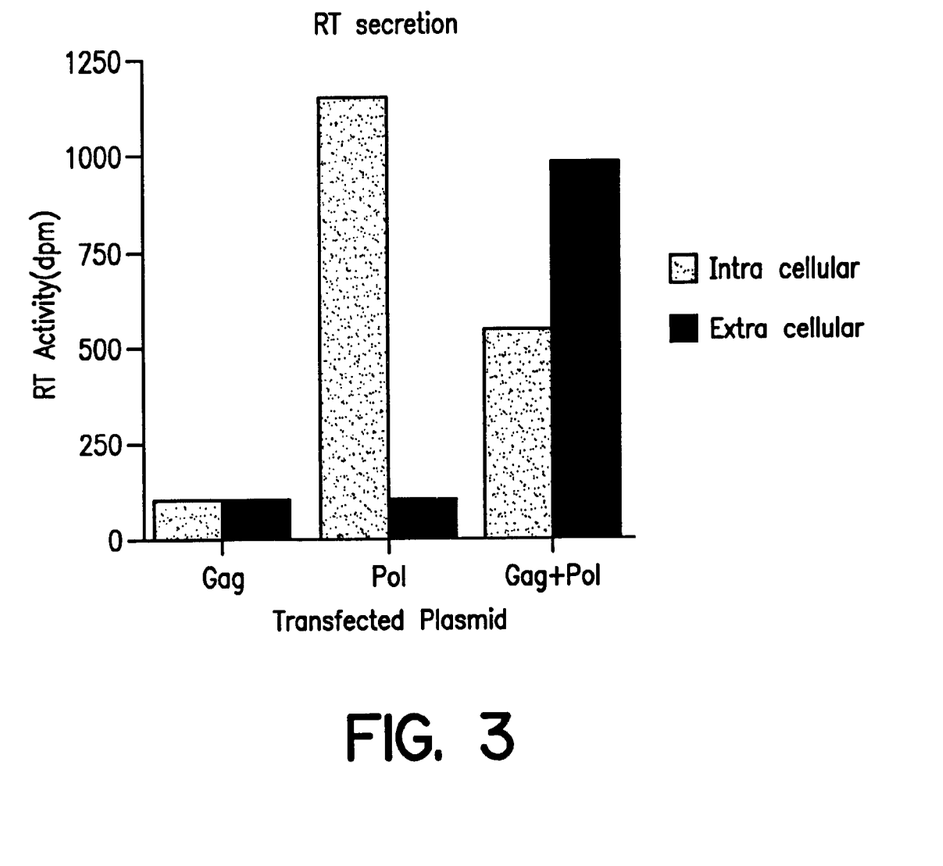
FIG. 3 sets forth data confirming the reverse transcriptase (RT) activity of plasmids constructed according to the invention.

RT is a protein product of pol gene expression. Therefore, expression of pol in the pCMV-ΔG-P, pCMV-GP and pCMV-GΔP plasmids was confirmed in 293 cell lines by measuring reverse transcriptase (RT) activity in the transfected cells and conditioned cell medium (Example I. RT activity was detected in the conditioned medium of cells transfected with pCMV-GP (expressing gag and pol together), but was minimal in the medium of cells transfected with pCMV-GΔP (gag expressing) and pCMV-ΔG-P (pol expressing) (FIG. 3). In contrast, intracellular RT activity was high in the pCMV-ΔG-P transfected cells, but minimal in the pCMV-GΔP transfected cells (id.). The latter data confirm that the pCMV-ΔG-P transfected cells express pol, but do not experience a significant degree of the gag-pol protein association that is preparatory to virion assembly.

However, when produced in a cell line in the presence of a provirus (the LZRNL provirus integrated into the 293 cell lines) and an env expressing plasmid (pVSV-G), the separate expression of gag, pol and env from, respectively, pCMV-GΔP, pCMV-ΔG-P and pCMV-G (expresses the env gene of the vesticular stomatitis virus, VSV) supply the gag, pol and env functions required for production of LZRNL retrovirus vector. Although intracellular pol levels remained higher than pol levels obtained in cell lines transfected with pVSV-G and a gag-pol expressing plasmid (the "associated gag-pol" cell line), viral titers obtained from the cells transfected with pVSV-G, pCMV-GΔP and pCMV-ΔG-P (the "disassociated gag pol" cell line) are not substantially less than the titers obtainable from the associated gag-pol cell line (Example I). The data obtained in this comparison are:

| Transfecting Plasmid | RT/Medium | RT/Cell Lysate | Virus Titer |
| --- | --- | --- | --- |
| pCMV-G (env) | 263 | 253 | <1 |
| pCMV-G (env) + pCMV-GP (gag-pol) | 3873 | 933 | $1 \times 10^5$ |
| pCMV-G (env) + pCMV-GΔP (gag) + pCMV-ΔG-P (pol) | 434 | 1790 | $1 \times 10^3$ |

The increase in the number of recombination events necessary to produce RCR from the disassociated gag pol packaging cell lines in turn decreases the likelihood that RCRs will be produced, thus enhancing the safety of the vector production system. The separation of genes encoding each structural protein (gag, pol and env) into different expression units also enables use of the inventive vector production system to construct chimeric retroviruses having structural protein components from different parent species.

For example, using the separation techniques of the invention, a plasmid expressing MoMLV gag or pol can be combined in a cell line with a plasmid expressing pol or gag from another retrovirus species; e.g., HIV-1 (Example II). Such chimeric retroviruses have unique targeting capabilities defined by the capabilities of the component structural proteins. For example, the ability to infect non-dividing cells possessed by HIV-1 (Weinberg, et al., *J.Exp.Med.*, 174:1477–1482 (1991)) is conferred on a packaging cell line based on a well-characterized murine or avian retrovirus, such as MoMLV or ALV, by transfection of a suitable cell line with plasmids which supply, respectively, pol and gag from HIV-1 and the murine or avian retrovirus.

A further use for the retrovirus production system of the invention is in enhancing the activity of retroviral vectors by supplying increased expression of gag or pol, as needed. For example, a packaging cell line in which vector production is limited by insufficient expression of pol achieves increased vector production on addition of a plasmid expressing only pol.

To these ends, the retrovirus production system described may be modified using, for example, genes encoding structural proteins of different retrovirus species than those specifically noted above, different expression plasmids (e.g., having different promoters and detectable markers) than those specifically noted above, and different cell lines than those specifically noted above for transfection with gag and pol plasmids constructed according to the invention. Those of ordinary skill in the art will be familiar with, or may readily ascertain, the identity of such other species, plasmids and cell lines.

For example, particularly useful promoters can be switched "on" or "off" to confirm and control gene expression in the vector production system. Examples of such promoters are the antibiotic inducible and ligand inducible nuclear receptor promoters. With respect to the latter, nuclear receptors represent a family of transcriptional enhancer factors that act by binding to specific DNA sequences found in target promoters known as response elements. Specific members of the nuclear receptor family include the primary intracellular targets for small lipid-soluble ligands, such as vitamin $D_3$ and retinoids, as well as steroid and thyroid hormones ("activating ligands").

Nuclear receptors activated by specific activating ligands are well suited for use as promoters in eukaryotic expression vectors since expression of genes can be regulated simply by controlling the concentration of ligand available to the receptor. For example, glucocorticoid-inducible promoters such as that of the long terminal repeat of the mouse mammary tumor virus (MMTV) have been widely used in this regard because the glucocorticoid response elements are expressed in a wide variety of cell types. One expression system which exploits glucocorticoid response elements responsive to a wide variety of steroid hormones (e.g., dexamethasone and progesterone) is a pGREtk plasmid (containing one or more rat tyrosine amino transferase glucocorticoid response elements upstream of the herpes simplex virus thymidine kinase (tk) promoter in pBLCAT8+), transfected in HeLa cells (see, Mader and White, *Proc. Natl. Acad. Sci USA*, 90:5603–5607, 1993 [pGRE2tk]; and, Klein-Hitpass, et al., *Cell*, 46:1053–1061, 1986 [pBLCAT8+]; the disclosures of which are incorporated herein by this reference to illustrate knowledge in the art concerning construction of suitable promoters derived from nuclear receptor response elements ["NRRE promoters"]).

Another particularly suitable NRRE promoter for use in the invention is one which is inducible by the vitamin $D_3$ compound 1,25-dihydroxyvitamin $D_3$ and non-hypercalcemic analogs thereof (collectively, "vitamin $D_3$ activating ligands"). NRRE promoters inducible by vitamin $D_3$ activating ligands contain the vitamin $D_3$ receptor (VDR) response elements PurG(G/T)TCA which recognizes direct repeats separated by 3 base pairs. Vitamin $D_3$ response elements are found upstream of human osteocalcin and mouse osteopontin genes; transcription of these genes is activated on binding of the VDR (see, e.g., Morrison and Eisman, *J. Bone Miner. Res.*, 6:893–899 (1991); and, Ferrara, et al., *J. Biol. Chem.*, 269:2971–2981 (1994)), the disclosures of which are incorporated herein by this reference to illustrate knowledge in the art of vitamin $D_3$ responsive inducible promoters). Recent experimental results from testing of a recombinant expression vector containing the mouse osteopontin VDR upstream of a truncated herpes simplex virus thymidine kinase (tk) promoter suggested that 9-cis-retinoic acid can augment the response of VDR to 1,25-hydroxyvitamin $D_3$ (see, Carlberg, et al., *Nature*, 361:657–660 (1993)).

Another well-characterized "on/off" switch for use in a recombinant expression vector is the antibiotic regulated promoter system. Means for construction of such a system are well-known in the art; for review in this regard, those of skill in the art may wish to consult Furth, (tetracycline control of cardiac gene expression); and, Niwa, et aL, *Gene*, 108:193–200 (1991) (use of the promoter system for high-expression transfectants).

Examples illustrating the practice of the invention are set forth below. These examples should not be regarded as limiting the scope of the invention, which will be defined by claims. Standard abbreviations (e.g., "ml" for milliliters, "h" for hours) are used throughout the examples. All references cited are incorporated herein.

EXAMPLE 1

RT ACTIVITY AND VIRAL TITERS PRODUCED IN THE RETROVIRAL PRODUCTION SYSTEM OF THE INVENTION pCMV-VSV-G, pCMV-GP, pCMV-ΔG-P and pCMV-GΔP were transfected into 293GP-LZRNL cell lines in the presence of 8 mg/ml polybrene. The cell line 293GP-LZRNL is a 293GP cell line that contains an integrated LZRNL provirus (LTR-lacZ-RSV-neoR-LTR) (Xu, et al., *Virology*, 171: 331–341 (1989)). The cell line 293GP-LZRNL/amphotropic is a 293GP-LZRNL cell line which also expresses the Moloney amphotropic envelope from a stably transfected amphotropic envelope expression plasmid (Sharma, et al. *Proc. Natl. Acad. Sci. USA.*, 93: 11842–11847 (1996)). pCMV-VSV-G expresses VSV-G from the strong HCMV promoter (Yee, et al., *Proc. Natl. Acad. Sci. USA*. 91: 9564–9568 (1994)).

The RT activity of virus produced from the transfected cell lines described in Table I was assayed by established methods (see, e.g., Goff, et al, *J. ViroL*, 38: 239–248 (1981)). A reaction volume of 100 ml RT reaction mixture contained; 50 mM Tris-HCl, pH8.3, 10 mM DTT, 1 mM $MnCl_2$, 60 mM NaCl, 20 mM dTTP, 2.5mCi $^3$HdTTP, 0.25% NP40 and 0.04 units of poly(rA)·p(dT)$_{10}$. The reaction mixture was incubated at 37° C. for 30 minutes, spotted onto filter paper disks and dried. The filter discs were washed with 5% $Na_2HPO_4$, water and finally rinsed with ethanol, dried and counted in scintillation counter.

Viral titers from vector production system of the invention were measured in the conditioned medium of the transfected cells by infecting rat 208F fibroblast cells with aliquots of the conditioned medium and selecting infected cells with G-148 as described in Miyanohara, et al., *Proc. Natl. Sci. USA*, 85:6538–6542 (1988).

Results of these assays are shown in Table I, above.

EXAMPLE II

VECTOR PRODUCTION SYSTEM FOR CHIMERIC RETROVIRUS VECTORS

Figure 4:
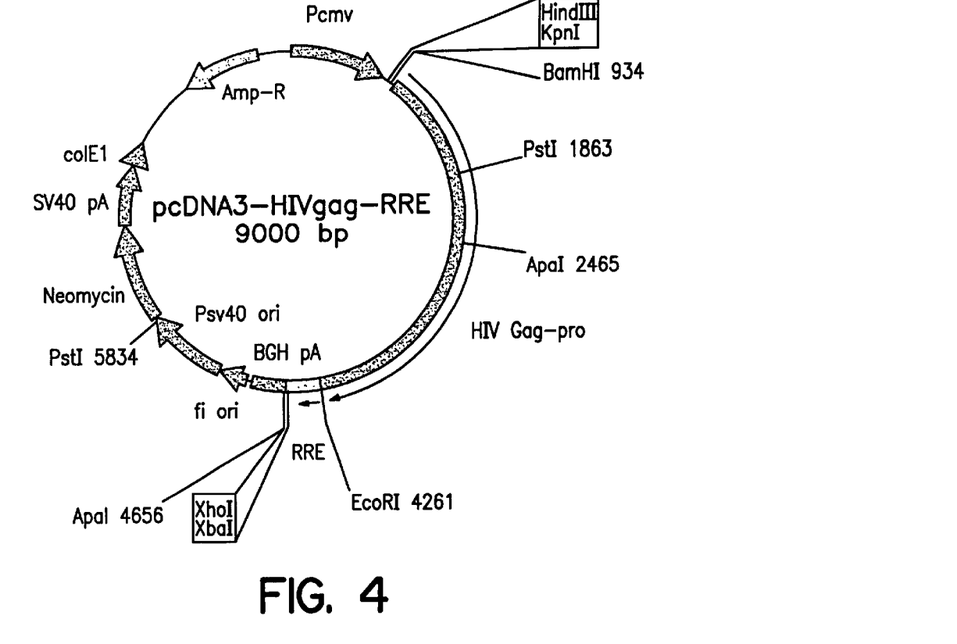
FIG. 4 is a map of the pcDNA3-HIVgag-RRE plasmid.

To construct a retrovirus capable of transfecting non-dividing cells, a chimera comprising gag from HIV-1 and pol from MoMLV was constructed as follows:

As a starting material, HIV gag and RRE (rev response element) sequences were inserted into plasmid pcDNA3 (Invitrogen). The HIV sequences inserted consist of a 3324 bp HIV-1 fragment from the SacI (at 486) to the EcoRI (at 5742) restriction sites in the HIV-1 genome, including the 238 bp RRE sequence (at 7759–7997) and excluding a 1932 bp MscI fragment (at 2619–4551) to form pcDNA3-HIVgag-RRE (FIG. 4). The nucleotide locations given for the HIV-1 genome correspond to the HIV-1 NL4-3 sequence (GenBank Accession No. M19921; SEQ.ID.No. 6). The HIV-1 gag fragment was obtained according to the method of the invention.

Figure 5:
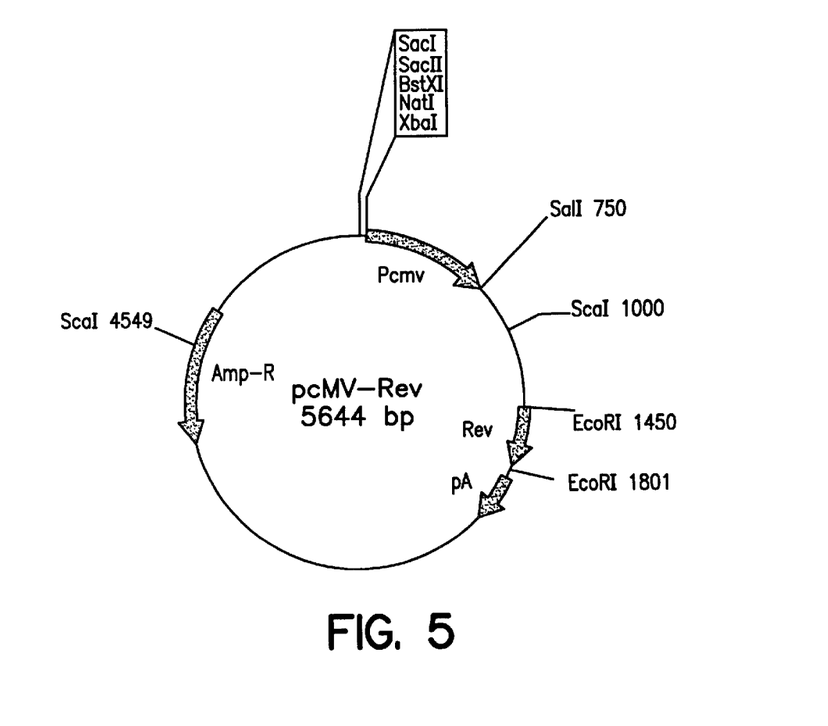
FIG. 5 is a map of the pCMV-Rev plasmid.

To provide rev, a 351 bp EcoRI fragment encoding HIV-1 rev cDNA was inserted into the EcoRI site of the pCMV-Bam plasmid (Yee, et al., *Proc. Nat'l. Acad. Sci. USA*, 91:9564–9568 (1994)) to form pCMV-rev (FIG. 5).

Figure 6:
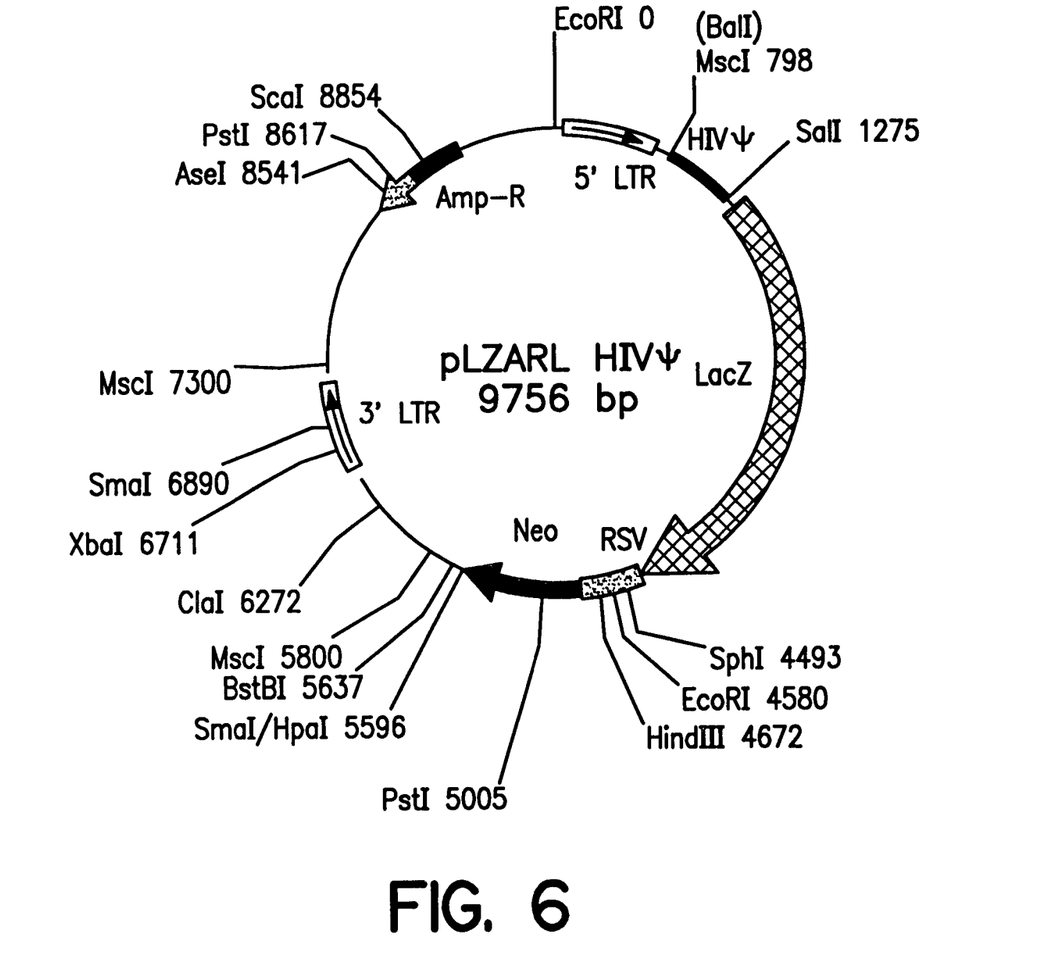
FIG. 6 is a map of the pLZRNL$_{HIV\psi}$ plasmid.

To provide the HIV packaging signal, the MoMLV packaging signal (located between the MscI and SalI restriction sites in the pLZRNL plasmid) was replaced with a 447 bp fragment containing the HIV-1 packaging signal (bp 632–1079) to form pLZRN$_{HIV\psi}$ (FIG. 6).

Transfection of 293 kidney cells with the plasmids was performed as described in Example I. Chimeric virus titers of 10–20 cfu/ml were obtained using the described constructs.

The invention having been fully described, modifications thereof and other uses therefor will likely be apparent to those of ordinary skill in the art. All such modifications and other uses should be considered as being included within the scope of the invention.

SUMMARY OF SEQUENCES

SEQ.ID.No. 1 is the nucleotide sequence of the MoMLV retrovirus (GenBank Accession No. J02255).

SEQ.ID.No. 2 is the nucleotide sequence of the gag gene of the MoMLV retrovirus.

SEQ.ID.No. 3 is the nucleotide sequence of the pol gene of the MoMLV retrovirus.

SEQ.ID.No. 4 is an oligonucleotide insert for the separate gag, pol coding plasmids of the invention.

SEQ.ID.No. 5 is an oligonucleotide insert for the separate gag, pol coding plasmids of the invention.

SEQ.ID.No. 6 is the nucleotide sequence of an HIV-1 clone described in GenBank Accession No. M19921.

The invention claimed is:

1. A method for producing replication-incompetent retrovirus vectors comprising transfecting cells with a first provirus plasmid that encodes gag, but not pol or envelope proteins; a second provirus plasmid that encodes pol, but not gag or envelope proteins; and a third separate envelope protein encoding construct.

2. The method of claim 1 wherein the first provirus plasmid is a provirus plasmid comprising an expressible polynucleotide sequence of SEQ ID NO: 2.

3. The method of claim 1 wherein the first provirus plasmid is pCMV-G-ΔP.

4. The method of claim 1, wherein said cells are from a packaging cell line.

5. The method of claim 1, wherein said envelope protein encoding construct has been stably transfected into said cells.

6. The method of claim 1, wherein said pol, gag and env proteins are all from the same parent virus.

7. The method of claim 1, wherein said pol, gag and env proteins are from 2 or more different parent viruses.

8. The method claim 1, wherein each of said pol, gag and env proteins are from different parent viruses.

9. A method for producing replication-incompetent retrovirus vectors comprising transfecting cells of a 293 human kidney cell line with pCMV-ΔG-P, pCMV-G-ΔP and a separate envelope encoding construct.

10. A method for producing replication-incompetent retrovirus vectors comprising transfecting cells of a 293 human kidney cell line with pcDNA3-HIVgag-RRE, pCMV-ΔG-P and a separate envelope encoding construct.

11. The method according to claim 9 wherein the cells are further transfected with pCMV-rev.

12. The method according to claim 9 wherein the cells are further transfected with pLZRNL$_{HIV\psi}$.

13. A retrovirus vector produced from a packaging cell line transfected with pCMV-ΔG-P, pCMV-G-ΔP and a separate envelope encoding construct.

14. A retrovirus vector produced from a packaging cell line transfected with pcDNA3-HIVgag-RRE, pCMV-ΔG-P and a separate envelope encoding construct.

15. The retrovirus vector of claim 14 wherein the packaging cell line is further transfected with pCMV-rev.

16. The retrovirus vector of claim 14 wherein the packaging cell line is further transfected with pLZRNL$_{HIV\psi}$.

* * * * *

SEQUENCE LISTING

<160> NUMBER OF SEQ ID NOS: 5

<210> SEQ ID NO 1
<211> LENGTH: 8332
<212> TYPE: DNA
<213> ORGANISM: Moloney murine leukemia virus (MoMLV)

<400> SEQUENCE: 1

| | | | | | |
|---|---|---|---|---|---|
| gcgccagtcc | tccgattgac | tgagtcgccc | gggtacccgt | gtatccaata aaccctcttg | 60 |
| cagttgcatc | cgacttgtgg | tctcgctgtt | ccttgggagg | gtctcctctg agtgattgac | 120 |
| tacccgtcag | cggggtgtctt | tcatttgggg | gctcgtccgg | gatcgggaga ccctgccca | 180 |
| gggaccaccg | acccaccacc | gggaggtaag | ctggccagca | acttatctgt gtctgtccga | 240 |
| ttgtctagtg | tctatgactg | attttatgcg | cctgcgtcgg | tactagttag ctaactagct | 300 |
| ctgtatctgg | cggacccgtg | gtggaactga | cgagttcgga | acacccggcc gcaaccctgg | 360 |
| gagacgtccc | agggacttcg | ggggccgttt | tgtggcccg | acctgagtcc aaaaatcccg | 420 |
| atcgttttgg | actctttggt | gcacccccct | tagaggaggg | atatgtggtt ctggtaggag | 480 |
| acgagaacct | aaaacagttc | ccgcctccgt | ctgaattttt | gctttcggtt tgggaccgaa | 540 |
| gccgcgccgc | gcgtcttgtc | tgctgcagca | tcgttctgtg | ttgtctctgt ctgactgtgt | 600 |
| ttctgtattt | gtctgagaat | atgggccaga | ctgttaccac | tcccttaagt ttgaccttag | 660 |
| gtcactggaa | agatgtcgag | cggatcgctc | acaaccagtc | ggtagatgtc aagaagagac | 720 |
| gttgggttac | cttctgctct | gcagaatggc | caacctttaa | cgtcggatgg ccgcgagacg | 780 |
| gcacctttaa | ccgagacctc | atcacccagg | ttaagatcaa | ggtcttttca cctggcccgc | 840 |
| atggacaccc | agaccaggtc | ccctacatcg | tgacctggga | agccttggct tttgacccc | 900 |
| ctccctgggt | caagcccttt | gtacacccta | agcctccgcc | tcctcttcct ccatccgccc | 960 |
| cgtctctccc | ccttgaacct | cctcgttcga | ccccgcctcg | atcctccctt tatccagccc | 1020 |
| tcactccttc | tctaggcgcc | aaacctaaac | ctcaagttct | ttctgacagt ggggggccgc | 1080 |
| tcatcgacct | acttacagaa | gacccccgc | cttataggga | cccaagacca cccccttccg | 1140 |
| acagggacgg | aaatggtgga | gaagcgaccc | ctgcgggaga | ggcaccggac ccctccccaa | 1200 |
| tggcatctcg | cctacgtggg | agacgggagc | cccctgtggc | cgactccact acctcgcagg | 1260 |
| cattccccct | ccgcgcagga | ggaaacggac | agcttcaata | ctggccgttc tcctcttctg | 1320 |
| acctttacaa | ctggaaaaat | aataaccctt | cttttctga | agatccaggt aaactgacag | 1380 |
| ctctgatcga | gtctgttctc | atcacccatc | agcccacctg | gacgactgt cagcagctgt | 1440 |
| tggggactct | gctgaccgga | gaagaaaaac | aacgggtgct | cttagaggct agaaaggcgg | 1500 |
| tgcgggggcga | tgatgggcgc | cccactcaac | tgcccaatga | agtcgatgcc gcttttcccc | 1560 |
| tcgagcgccc | agactgggat | tacaccaccc | aggcaggtag | gaaccaccta gtccactatc | 1620 |
| gccagttgct | cctagcgggt | ctccaaaacg | cgggcagaag | ccccaccaat ttggccaagg | 1680 |
| taaaggaat | aacacaaggg | cccaatgagt | ctccctcggc | cttcctagag agacttaagg | 1740 |
| aagcctatcg | caggtacact | ccttatgacc | ctgaggaccc | aggcaagaa actaatgtgt | 1800 |
| ctatgtcttt | catttggcag | tctgccccag | acattgggag | aaagttagag aggttagaag | 1860 |
| atttaaaaaa | caagacgctt | ggagatttgg | ttagagaggc | agaaaagatc tttaataaac | 1920 |
| gagaaaccccc | ggaagaaaga | gaggaacgta | tcaggagaga | aacagaggaa aaagaagaac | 1980 |
| gccgtaggac | agaggatgag | cagaaagaga | aagaaagaga | tcgtaggaga catagagaga | 2040 |

-continued

```
tgagcaagct attggccact gtcgttagtg gacagaaaca ggatagacag ggaggagaac    2100
gaaggaggtc ccaactcgat cgcgaccagt gtgcctactg caaagaaaag gggcactggg    2160
ctaaagattg tcccaagaaa ccacgaggac ctcggggacc aagaccccag acctccctcc    2220
tgaccctaga tgactaggga ggtcaggggtc aggagccccc ccctgaaccc aggataaccc    2280
tcaaagtcgg ggggcaaccc gtcaccttcc tggtagatac tggggcccaa cactccgtgc    2340
tgacccaaaa tcctggaccc ctaagtgata agtctgcctg gtccaagggg ctactggag     2400 gaaagcggta tcgctggacc acggatcgca aagtacatct agctaccggt aaggtcaccc    2460
actctttcct ccatgtacca gactgtccct atcctctgtt aggaagagat ttgctgacta    2520
aactaaaagc ccaaatccac tttgagggat caggagctca ggttatggga ccaatggggc    2580
agcccctgca agtgttgacc ctaaatatag aagatgagca tcggctacat gagacctcaa    2640
aagagccaga tgtttctcta gggtccacat ggctgtctga ttttcctcag gcctgggcgg    2700
aaaccggggg catgggactg gcagttcgcc aagctcctct gatcatacct ctgaaagcaa    2760
cctctacccc cgtgtccata aaacaatacc ccatgtcaca agaagccaga ctggggatca    2820
agccccacat acagagactg ttggaccagg gaatactggt accctgccag tcccctgga     2880 acacgccccc gctacccgtt aagaaaccag ggactaatga ttataggcct gtccaggatc    2940
tgagagaagt caacaagcgg gtggaagaca tccacccac cgtgcccaac ccttacaacc      3000
tcttgagcgg gctcccaccg tcccaccagt ggtacactgt gcttgattta aaggatgcct    3060
ttttctgcct gagactccac cccaccagtc agcctctctt cgcctttgag tggagagatc    3120
cagagatggg aatctcagga caattgacct ggaccagact cccacagggt ttcaaaaaca    3180 gtcccacct gtttgatgag gcactgcaca gagacctagc agacttccgg atccagcacc      3240
cagacttgat cctgctacag tacgtggatg acttactgct ggccgccact tctgagctag    3300
actgccaaca aggtactcgg gccctgttac aaaccctagg gaacctcggg tatcgggcct    3360
cggccaagaa agcccaaatt tgccagaaac aggtcaagta tctggggtat cttctaaaag    3420
agggtcagag atggctgact gaggccagaa aagagactgt gatggggcag cctactccga    3480
agacccctcg acaactaagg gagttcctag ggacggcagg cttctgtcgc ctctggatcc    3540
ctgggtttgc agaaatggca gcccccttgt accctctcac caaaacgggg actctgttta    3600
attggggccc agaccaacaa aaggcctatc aagaaatcaa gcaagctctt ctaactgccc    3660
cagccctggg gttgccagat ttgactaagc cctttgaact cttttgtcgac gagaagcagg    3720 gctacgccaa aggtgtccta acgcaaaaac tgggaccttg gcgtcggccg gtggcctacc    3780
tgtccaaaaa gctagaccca gtagcagctg ggtggccccc ttgcctacgg atggtagcag    3840
ccattgccgt actgacaaag gatgcaggca agctaaccat gggacagcca ctagtcattc    3900
tggcccccca tgcagtagag gcactagtca acaaccccc cgaccgctgg ctttccaacg    3960
cccggatgac tcactatcag gccttgcttt tggacacgga ccgggtccag ttcggaccgg    4020 tggtagcccct gaacccggct acgctgctcc cactgcctga ggaagggctg caacacaact    4080
gccttgatat cctggccgaa gcccacggaa cccgacccga cctaacggac cagccgctcc    4140
cagacgccga ccacacctgg tacacggatg gaagcagtct cttacaagag ggacagcgta    4200
aggcgggagc tgcggtgacc accgagaccg aggtaatctg ggctaaagcc ctgccagccg    4260
ggacatccgc tcagcgggct gaactgatag cactcaccca ggccctaaag atggcagaag    4320
gtaagaagct aaatgtttat actgatagcc gttatgcttt tgctactgcc catatccatg    4380
```

-continued

```
gagaaatata cagaaggcgt gggttgctca catcagaagg caaagagatc aaaaataaag    4440
acgagatctt ggccctacta aaagccctct ttctgcccaa aagacttagc ataatccatt    4500
gtccaggaca tcaaagggga cacagcgccg aggctagagg caaccggatg ctgaccaag     4560 cggcccgaaa ggcagccatc acagagactc cagacacctc taccctcctc atagaaaatt    4620
catcacccta cacctcagaa catttttcatt acacagtgac tgatataaag gacctaacca   4680
agttgggggc catttatgat aaaacaaaga agtattgggt ctaccaagga aaacctgtga    4740
tgcctgacca gtttactttt gaattattag actttcttca tcagctgact cacctcagct    4800
tctcaaaaat gaaggctctc ctagagagaa gccacagtcc ctactacatg ctgaaccggg    4860
atcgaacact caaaaatatc actgagacct gcaaagcttg tgcacaagtc aacgccagca    4920
agtctgccgt taaacaggga actagggtcc gcgggcatcg gcccggcact cattgggaga    4980
tcgatttcac cgagataaag cccggattgt atggctataa atatcttcta gttttttatag   5040 ataccttttc tggctggata aagccttcc caaccaagaa agaaaccgcc aaggtcgtaa     5100
ccaagaagct actagaggag atcttcccca ggttcggcat gcctcaggta ttgggaactg    5160
acaatgggcc tgccttcgtc tccaaggtga gtcagacagt ggccgatctg ttggggattg    5220
attggaaatt acattgtgca tacagacccc aaagctcagg ccaggtagaa agaatgaata    5280
gaaccatcaa ggagacttta actaaattaa cgcttgcaac tggctctaga gactgggtgc    5340
tcctactccc cttagccctg taccgagccc gcaacacgcc gggcccccat ggcctcaccc    5400
catatgagat cttatatggg gcaccccgc cccttgtaaa cttccctgac cctgacatga     5460
caagagttac taacagcccc tctctccaag ctcacttaca ggctctctac ttagtccagc    5520
acgaagtctg gagacctctg gcggcagcct accaagaaca actggaccga ccgtggtac     5580 ctcacccta ccgagtcggc gacacagtgt gggtccgccg acaccagact aagaacctag     5640
aacctcgctg gaaaggacct tacacagtcc tgctgaccac ccccaccgcc ctcaaagtag    5700
acggcatcgc agcttggata cacgccgccc acgtgaaggc tgccgacccc ggggtggac     5760 catcctctag actgacatgg cgcgttcaac gctctcaaaa cccttaaaa ataaggttaa     5820 cccgcgaggc cccctaatcc ccttaattct tctgatgctc agagggtca gtactgcttc     5880 gcccggctcc agtcctcatc aagtctataa tatcacctgg gaggtaacca atggagatcg    5940
ggagacggta tgggcaactt ctggcaacca ccctctgtgg acctggtggc ctgaccttac    6000
cccagattta tgtatgttag cccaccatgg accatcttat tggggctag aatatcaatc     6060 cccttttttct tctccccgg ggccccttg ttgctcaggg ggcagcagcc caggctgttc     6120
cagagactgc gaagaacctt taacctccct caccctcgg tgcaacactg cctgaacag      6180 actcaagcta gaccagacaa ctcataaatc aaatgaggga ttttatgttt gccccgggcc    6240
ccaccgcccc cgagaatcca agtcatgtgg ggtccagac tccttctact gtgcctattg     6300
gggctgtgag acaaccggta gagcttactg gaagccctcc tcatcatggg atttcatcac    6360
agtaaacaac aatctcacct ctgaccaggc tgtccaggta tgcaaagata taagtggtg     6420 caaccccta gttattcggt ttacagacgc cgggagacgg gttacttcct ggaccacagg    6480
acattactgg ggcttacgtt tgtatgtctc cggacaagat ccaggggctta catttgggat   6540 ccgactcaga taccaaaatc taggacccg cgtcccaata gggccaaacc ccgttctggc     6600
agaccaacag ccactctcca agcccaaacc tgttaagtcg ccttcagtca ccaaaccacc    6660
cagtgggact cctctctccc ctaccaact tccaccggcg ggaacggaaa ataggctgct     6720
aaacttagta gacggagcct accaagccct caacctcacc agtcctgaca aaacccaaga   6780
```

-continued

| | |
|---|---|
| gtgctggttg tgtctagtag cgggacccccc ctactacgaa ggggttgccg tcctgggtac | 6840 |
| ctactccaac catacctctg ctccagccaa ctgctccgtg gcctcccaac acaagttgac | 6900 |
| cctgtccgaa gtgaccggac agggactctg cataggagca gttcccaaaa cacatcaggc | 6960 |
| cctatgtaat accacccaga caagcagtcg agggtcctat tatctagttg ccctacagg | 7020 |
| taccatgtgg gcttgtagta ccgggcttac tccatgcatc tccaccacca tactgaacct | 7080 |
| taccactgat tattgtgttc ttgtcgaact ctggccaaga gtcacctatc attcccccag | 7140 |
| ctatgtttac ggcctgtttg agatccaa ccgacacaaa agagaaccgg tgtcgttaac | 7200 |
| cctggcccta ttattgggtg gactaaccat ggggggaatt ccgctggaa taggaacagg | 7260 |
| gactactgct ctaatggcca ctcagcaatt ccagcagctc caagccgcag tacaggatga | 7320 |
| tctcagggag gttgaaaaat caatctctaa cctagaaaag tctctcactt ccctgtctga | 7380 |
| agttgtccta cagaatcgaa ggggcctaga cttgttattt ctaaaagaag gagggctgtg | 7440 |
| tgctgctcta aaagaagaat gttgcttcta tgcggaccac acaggactag tgagagacag | 7500 |
| catggccaaa ttgagagaga ggcttaatca gagacagaaa ctgtttgagt caactcaagg | 7560 |
| atggtttgag ggactgttta acagatcccc ttggtttacc accttgatat ctaccattat | 7620 |
| gggaccctc attgtactcc taatgatttt gctcttcgga ccctgcattc ttaatcgatt | 7680 |
| agtccaattt gttaaagaca ggatatcagt ggtccaggct ctagtttga ctcaacaata | 7740 |
| tcaccagctg aagcctatag agtacgagcc atagataaaa taaagatttt tatttagtct | 7800 |
| ccagaaaaag gggggaatga agaccccac ctgtaggttt ggcaagctag cttaagtaac | 7860 |
| gccattttgc aaggcatgga aaatacata actgagaata gagaagttca gatcaaggtc | 7920 |
| aggaacagat ggaacagctg aatatgggcc aaacaggata tctgtggtaa gcagttcctg | 7980 |
| ccccggctca gggccaagaa cagatggaac agctgaatat gggccaaaca ggatatctgt | 8040 |
| ggtaagcagt tcctgccccg gctcagggcc aagaacagat ggtccccaga tgcggtccag | 8100 |
| ccctcagcag tttctagaga accatcagat gtttccaggg tgccccaagg acctgaaatg | 8160 |
| accctgtgcc ttatttgaac taaccaatca gttcgcttct cgcttctgtt cgcgcgcttc | 8220 |
| tgctccccga gctcaataaa agagcccaca cccctcact cggggcgcca gtcctccgat | 8280 |
| tgactgagtc gcccgggtac ccgtgtatcc aataaaccct cttgcagttg ca | 8332 |

<210> SEQ ID NO 2
<211> LENGTH: 1617
<212> TYPE: DNA
<213> ORGANISM: Moloney murine leukemia virus (MoMLV)

<400> SEQUENCE: 2

| | |
|---|---|
| atgggccaga ctgttaccac tcccttaagt ttgaccttag gtcactggaa agatgtcgag | 60 |
| cggatcgctc acaaccagtc ggtagatgtc aagaagagac gttgggttac cttctgctct | 120 |
| gcagaatggc caacctttaa cgtcggatgg ccgcgagacg caccttttaa ccgagacctc | 180 |
| atcacccagg ttaagatcaa ggtcttttca cctggcccgc atggacaccc agaccaggtc | 240 |
| ccctacatcg tgacctggga agccttggct tttgaccccc ctccctgggt caagcccttt | 300 |
| gtacacccta agcctccgcc tcctcttcct ccatccgccc cgtctctccc cttgaacct | 360 |
| cctcgttcga ccccgcctcg atcctccctt tatccagccc tcactccttc tctaggcgcc | 420 |
| aaacctaaac tcaagttctc ttctgacagt ggggggccgc tcatcgacct acttacagaa | 480 |
| gaccccccgc cttataggga cccaagacca ccccctttcccg acagggacgg aaatggtgga | 540 |

-continued

```
gaagcgaccc ctgcgggaga ggcaccggac ccctccccaa tggcatctcg cctacgtggg      600
agacgggagc ccctgtggc cgactccact acctcgcagg cattccccct ccgcgcagga      660
ggaaacggac agcttcaata ctggccgttc tcctcttctg acctttacaa ctggaaaaat      720
aataaccctt cttttttctga agatccaggt aaactgacag ctctgatcga gtctgttctc      780
atcacccatc agcccacctg ggacgactgt cagcagctgt gggggactct gctgaccgga      840
gaagaaaaac aacgggtgct cttagaggct agaaaggcgg tgcggggcga tgatgggcgc      900
cccactcaac tgcccaatga agtcgatgcc gcttttcccc tcgagcgccc agactgggat      960
tacaccaccc aggcaggtag gaaccaccta gtccactatc gccagttgct cctagcgggt     1020
ctccaaaacg cgggcagaag ccccaccaat ttggccaagg taaaaggaat aacacaaggg     1080
cccaatgagt ctccctcggc cttcctagag agacttaagg aagcctatcg caggtacact     1140
ccttatgacc ctgaggaccc agggcaagaa actaatgtgt ctatgtcttt catttggcag     1200
tctgccccag acattgggag aaagttagag aggttagaag atttaaaaaa caagacgctt     1260
ggagatttgg ttagagaggc agaaaagatc tttaataaac gagaaccccc ggaagaaaga     1320
gaggaacgta tcaggagaga aacagaggaa aaagaagaac gccgtaggac agaggatgag     1380
cagaaagaga aagaaagaga tcgtaggaga catagagaga tgagcaagct attggccact     1440
gtcgttagtg gacagaaaca ggatagacag ggaggagaac gaaggaggtc ccaactcgat     1500
cgcgaccagt gtgcctactg caaagaaaag gggcactggg ctaaagattg tcccaagaaa     1560
ccacgaggac ctcggggacc aagacccag acctccctcc tgaccctaga tgactag         1617
```

<210> SEQ ID NO 3
<211> LENGTH: 3612
<212> TYPE: DNA
<213> ORGANISM: Moloney murine leukemia virus (MoMLV)

<400> SEQUENCE: 3

```
accctagatg actagggagg tcagggtcag gagcccccc ctgaacccag gataaccctc        60
aaagtcgggg ggcaacccgt caccttcctg gtagatactg ggcccaaca ctccgtgctg       120 acccaaaatc ctggaccccct aagtgataag tctgcctggg tccaagggc tactggagga       180 aagcggtatc gctggaccac ggatcgcaaa gtacatctag ctaccggtaa ggtcacccac       240
tctttcctcc atgtaccaga ctgtccctat cctctgttag aagagatttt gctgactaaa       300
ctaaaagccc aaatccactt tgagggatca ggagctcagg ttatgggacc aatggggcag       360
cccctgcaag tgttgaccct aaatatagaa gatgagcatc ggctacatga acctcaaaa       420 gagccagatg tttctctagg gtccacatgg ctgtctgatt tcctcaggc ctgggcggaa       480 accgggggca tgggactggc agttcgccaa gctcctctga tcatacctct gaaagcaacc       540
tctacccccg tgtccataaa acaataccccc atgtcacaag aagccagact ggggatcaag       600
ccccacatac agagactgtt ggaccaggga atactggtac cctgccagtc ccctggaac       660 acgccctgc taccgttaa gaaccaggg actaatgatt ataggcctgt ccaggatctg       720
agagaagtca caagcgggt ggaagacatc caccccaccg tgcccaaccc ttacaacctc       780
ttgagcgggc tcccaccgtc ccaccagtgg tacactgtgc ttgatttaaa ggatgccttt       840
ttctgcctga gactccaccc caccagtcag cctctcttcg cctttgagtg gagagatcca       900
gagatgggaa tctcaggaca attgacctgg accagactcc cacagggttt caaaaacagt       960 cccacccctgt tgatgaggc actgcacaga gacctagcag acttccggat ccagcaccca     1020
gacttgatcc tgctacagta cgtggatgac ttactgctgg ccgccacttc tgagctagac      1080
```

```
tgccaacaag gtactcgggc cctgttacaa accctaggga acctcgggta tcgggcctcg      1140
gccaagaaag cccaaatttg ccagaaacag gtcaagtatc tggggtatct tctaaaagag      1200
ggtcagagat ggctgactga ggccagaaaa gagactgtga tggggcagcc tactccgaag      1260
acccctcgac aactaaggga gttcctaggg acggcaggct tctgtcgcct ctggatccct      1320
gggtttgcag aaatggcagc cccttgtac cctctcacca aaacgggac tctgtttaat       1380 tggggcccag accaacaaaa ggcctatcaa gaaatcaagc aagctcttct aactgcccca      1440 gccctgggt tgccagattt gactaagccc tttgaactct ttgtcgacga aagcagggc        1500 tacgccaaag gtgtcctaac gcaaaaactg gaccttggc gtcggccggt ggcctacctg      1560
tccaaaaagc tagacccagt agcagctggg tggccccctt gcctacggat ggtagcagcc      1620
attgccgtac tgacaaagga tgcaggcaag ctaaccatgg acagccact agtcattctg      1680 gccccccatg cagtagaggc actagtcaaa caaccccccg accgctggct ttccaacgcc      1740
cggatgactc actatcaggc cttgcttttg gacacggacc gggtccagtt cggaccggtg      1800
gtagccctga acccggctac gctgctccca ctgcctgagg aagggctgca acacaactgc      1860
cttgatatcc tggccgaagc ccacggaacc cgacccgacc taacggacca gccgctccca      1920
gacgccgacc acacctggta cacggatgga agcagtctct acaagagggg acagcgtaag      1980
gcgggagctg cggtgaccac cgagaccgag gtaatctggg ctaaagccct gccagccggg      2040
acatccgctc agcgggctga actgatagca ctcacccagg ccctaaagat ggcagaaggt      2100
aagaagctaa atgtttatac tgatagccgt tatgcttttg ctactgccca tatccatgga      2160
gaaatataca gaaggcgtgg gttgctcaca tcagaaggca aagagatcaa aaataaagac      2220
gagatcttgg ccctactaaa agccctcttt ctgcccaaaa gacttagcat aatccattgt      2280
ccaggacatc aaaagggaca cagcgccgag gctagaggca accggatggc tgaccaagcg      2340
gcccgaaagg cagccatcac agagactcca gacacctcta ccctcctcat agaaaattca      2400
tcaccctaca cctcagaaca ttttcattac acagtgactg atataaagga cctaaccaag      2460
ttgggggcca tttatgataa acaaagaag tattgggtct accaaggaaa acctgtgatg      2520
cctgaccagt ttactttga attattagac tttcttcatc agctgactca cctcagcttc      2580
tcaaaaatga aggctctcct agagagaagc cacagtccct actacatgct gaaccgggat      2640
cgaacactca aaatatcac tgagacctgc aaagcttgtg cacaagtcaa cgccagcaag      2700
tctgccgtta acagggaac tagggtccgc gggcatcggc ccggcactca ttgggagatc      2760
gatttcaccg agataaagcc cggattgtat ggctataaat atcttctagt ttttatagat      2820 acctttctg gctggataga agccttccca accaagaaag aaaccgccaa ggtcgtaacc      2880
aagaagctac tagaggagat cttccccagg ttcggcatgc ctcaggtatt gggaactgac      2940
aatgggcctg ccttcgtctc caaggtgagt cagacagtgg ccgatctgtt ggggattgat      3000
tggaaattac attgtgcata cagaccccaa agctcaggcc aggtagaaag aatgaataga      3060
accatcaagg agactttaac taaattaacg cttgcaactg gctctagaga ctgggtgctc      3120
ctactcccct tagccctgta ccgagcccgc aacacgccgg gccccatgg cctcacccca      3180 tatgagatct tatatgggc accccgccc cttgtaaact tccctgaccc tgacatgaca      3240
agagttacta acagcccctc tctccaagct cacttacagg ctctctactt agtccagcac      3300
gaagtctgga gacctctggc ggcagcctac caagaacaac tggaccgacc ggtggtacct      3360 caccccttacc gagtcggcga cacagtgtgg gtccgccgac accagactaa gaacctagaa      3420
```

-continued

```
cctcgctgga aaggacctta cacagtcctg ctgaccaccc ccaccgccct caaagtagac      3480
ggcatcgcag cttggataca cgccgcccac gtgaaggctg ccgacccgg gggtggacca       3540 tcctctagac tgacatggcg cgttcaacgc tctcaaaacc ccttaaaaat aaggttaacc     3600
cgcgaggccc cc                                                         3612
```

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 4
ttaaggtccc aactcgatcg                                                  20

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 5
ccagggttga gctagc                                                      16